United States Patent [19]

Swanson et al.

[11] Patent Number: 5,535,627
[45] Date of Patent: Jul. 16, 1996

[54] ROLL STRUCTURE ACOUSTIC GAGE AND METHOD

[75] Inventors: Ronald P. Swanson, Maplewood, Minn.; James K. Good; Richard L. Lowery, both of Stillwater, Okla.

[73] Assignee: The Board of Regents of Oklahoma State University, Stillwater, Okla.

[21] Appl. No.: 438,763

[22] Filed: May 11, 1995

Related U.S. Application Data

[63] Continuation of Ser. No. 182,375, Jan. 14, 1994, abandoned, which is a continuation of Ser. No. 878,386, Apr. 24, 1992, abandoned.

[51] Int. Cl.$^6$ ................................................. G01N 29/18
[52] U.S. Cl. ..................... 73/597; 73/12.05; 73/12.11; 73/78; 73/632
[58] Field of Search ...................... 73/597, 598, 594, 73/159, 78, 12.05, 12.11, 579, 632

[56] References Cited

U.S. PATENT DOCUMENTS

| | | | |
|---|---|---|---|
| 3,425,267 | 2/1969 | Pfeiffer | 73/78 |
| 3,540,270 | 11/1970 | Wolfer | 73/78 |
| 3,687,388 | 8/1972 | Pfeiffer | 242/534 |
| 4,218,922 | 8/1980 | Ensminger | 73/588 |
| 4,594,880 | 6/1986 | Murdoch et al. | 73/328 |
| 4,676,094 | 6/1987 | Hoffmann et al. | 73/78 |
| 4,845,989 | 6/1989 | Titlow et al. | 73/597 |

FOREIGN PATENT DOCUMENTS

| | | | |
|---|---|---|---|
| 397794 | 10/1973 | U.S.S.R. | 73/12 |

OTHER PUBLICATIONS

Pfeiffer, J. D., "Internal Pressures in a Wound Roll of Paper", Tappi Journal, vol. 49, No. 8, pp. 342–347.

Eriksson, L., "Deformations in Paper Rolls", Proceedings of the First Winding Technology Conference, pp. 195–212.

Hakiel, Z., "Nonlinear Model for Wound Roll Stresses", Tappi Journal, vol. 70, No. 5, pp. 113–117.

Kinsler, L. E. et al., "Fundamentals of Acoustics", 3rd ed.

Brillouin, L., "Wave Propagation and Group Velocity".

Altmann, H., "Formulas for Computing the Stresses in Center-Wound Rolls", Tappi Journal, vol. 51, No. 4, pp. 176–179.

Yagoda, H., "Generalized Formulas for Stresses in Wound Rolls", Tappi Journal, vol. 64, No. 2.

Good, J et al., "Predicting Internal Stresses in Center-Wound Rolls with An Undriven Nip Roller", Tappi Journal, vol. 74, No. 6, pp. 101–109.

*Primary Examiner*—Hezron E. Williams
*Assistant Examiner*—Nashmiya Ashraf
*Attorney, Agent, or Firm*—Head, Johnson & Kachigian

[57] ABSTRACT

A device and method for determining the radial pressure profile of a wound roll of material uses internal and external sensors to measure the time of flight of an acoustic wave induced within the roll by sharply impacting the surface, or by impacting a member in contact with the surface. The wave measurements are then fed to a computer which uses a modification of Hakiel's model to compute the radial pressure profile.

10 Claims, 3 Drawing Sheets

ROLL STRUCTURE ACOUSTIC GAGE AND METHOD

This is a continuation of application Ser. No. 08/182,375 filed on Jan. 14, 1994, now abandoned, which is a continuation of 07/873,386 filed on Apr. 24, 1992, also now abandoned.

BACKGROUND OF THE INVENTION

1. Field of the Invention

This invention relates to the general field of measurement and testing of wound roll structures. Roll structures are formed from "webs"-which may be any windable material, such as paper, plastic, film, fabric, coated laminates, composites, metal foil and the like. More specifically, this relates to measuring wave parameters within a roll and then analyzing the results to determine a radial pressure versus the roll radius.

2. Description of the Related Art

Most roll structure measurement is presently done with destructive and intrusive measuring devices. These are generally limited to research and development applications. The roll structure measurement techniques are usually qualitative and not quantitative. Examples include the Rhometer, Schmidt Hammer or even a calibrated thumb. Most quantitative techniques are intrusive and destructive, such as Force Sensitive Resistors (see Good, J. K. et al., "Predicting Internal Stresses in Center-Wound Rolls With An Undriven NIP Roller," and U.S. Pat. No. 4,594,880) and pull tabs. Other quantitative techniques, such as the density analyzer, require the rolls to be wound on special winders, with high precision measurement equipment attached. Some techniques only measure surface parameters (U.S. Pat. Nos. 3,425,267; 3,540,270).

Since many, if not most, web materials are stored and/or processed in a wound form, there is a need for a method and device to measure the internal parameters of the wound roll at any point or time in its formation, transport, storage or usage. As noted above, most methods to date are either destructive and invasive, or they only measure the surface parameters, or they are only measurable at the time of roll formation.

SUMMARY OF THE INVENTION

It is an object of this invention to provide a simple non-destructive and non-invasive means for measuring roll structure and stresses, which are generated within the wound material and at the core which, if not controlled, cause tearing, buckling core crushing or other defects.

It is a further object of this invention to provide a means for measuring roll structure that is compact, easy to move and operate, and accurate.

It is yet a further object of this invention to provide a device and method for generating and measuring wave propagation in a roll from which roll structure may be determined.

It is another object of this invention to provide a method and device for measuring roll structure that does not require knowledge of the winding tension.

It is an object of this invention to provide a method and device for generating and detecting waves in a roll structure.

It is an object of this invention to provide a method and device for measuring time of flight of waves generated within a laminate roll structure with variable modulus and deriving roll structure therefrom. Paper and plastic are particular examples of such structure or material to which the invention is applicable.

A mechanical pulser is placed in contact with the internal or external surface of a wound roll of material. In the following discussion, it is assumed the pulser is in contact with the exterior of the roll. This pulser comprises a tube with a projectile therein. One end of the pulser tube is attached to a pressurized air or gas source. The other end of the pulser tube has a spring loaded slidable plunger therein. A short burst of air or gas source is "fired" propelling the projectile through the pulser tube to impact the spring loaded plunger which is in contact with the roll surface. This impact creates a wave within the roll. There is a measuring device (such as a piezoelectric film, such as available under the mark KYNAR) that detects the entrance of the wave into the roll. The wave travels through the roll structure. Within the core of the roll, another sensor is located which detects the arrival of the wave from the surface. The signals from the surface measurement and the core measurement are sent to a computer, oscilloscope or other measuring and calculating device. The time of flight is measured by subtracting the time of wave arrival at the core, from the time of entrance of the wave at the surface. A roll model algorithm, derived from Hakiel's model is then used to calculate roll structure.

These objects are meant to be illustrative and not limiting. The manner of operation, novel features and further objectives and advantages of this invention may be better understood by reference to the accompanying drawings and description.

DESCRIPTION OF THE PREFERRED EMBODIMENT

Figure 1:
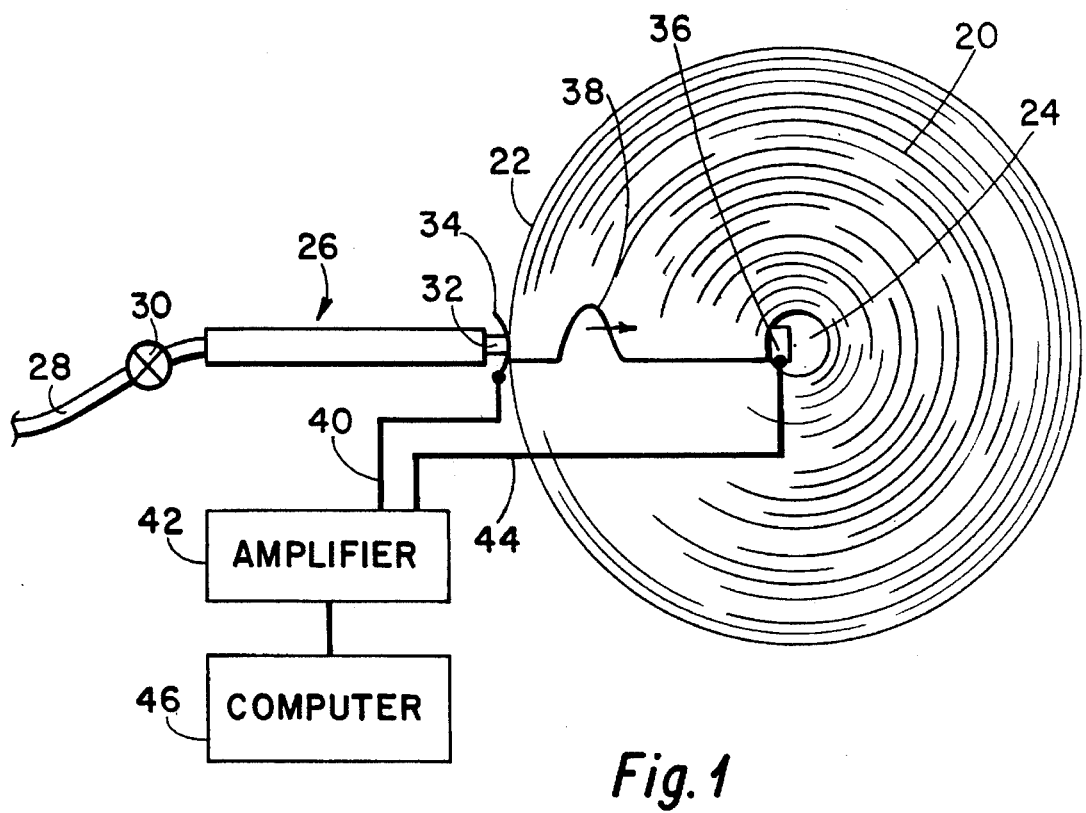
FIG. 1 is an elevational sideview of a roll with pulser applied.

FIG. 1 illustrates a roll 20 with an external surface 22 and a core 24. A pulser tube 26 is placed perpendicular or radially to the roll surface 22. One end of the pulser tube 26 has an attached air or gas tube 28 and a valve 30. The other end of the pulser tube 26 has a spring loaded plunger 32 in contact with the roll surface 22. A surface sensor 34 is placed at the plunger 32 roll surface 22 interface. In use, a projectile 52 (shown in FIGS. 2 and 3), is propelled by the pressurized air or gas through the pulser tube 26 and impacts the spring loaded plunger 32 creating a wave that enters the surface 22 of the roll 20. As the wave is generated, it is detected by the sensor 34 on the surface of the roll 22. When the wave reaches the core 24 of the roll, it is detected by a core sensor 36. One wave 38 is shown as an example traveling from the surface 22 to the core 24 of the roll. The wave detection by the surface sensor 34 creates a signal that travels by path 40 to an amplifier 42 or other detection/analyzing means. The wave detection by the core sensor 36 creates a signal that travels by path 44 to the amplifier 42 or other detection/ analyzing means. From the amplifier, the signals may be transmitted to a computer 46, oscilloscope or other recording/analyzing or print-out means. Filters (not shown) may be used if necessary. An amplifier may not be necessary. Alternatively, the signals may be fed to an oscilloscope then to a computer. The sensors may be of the KYNAR piezoelectric type, accelerometers or the like.

Although the above illustration has been done with a roll, it may also be used with a non-rolled stack or array of laminar material. The invention can be used during static or dynamic conditions of the roll.

Figure 2:
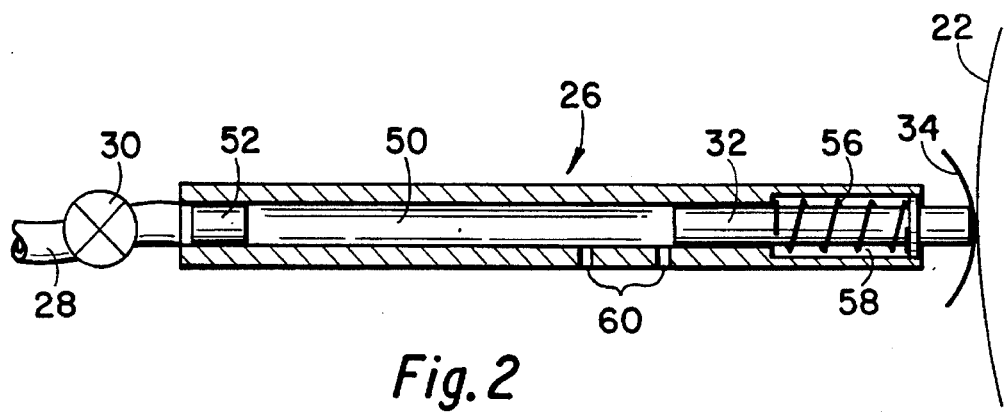
FIG. 2 is a cross-sectional sideview of the pulser with projectile in the "cocked" position.

FIG. 2 is a sectional sideview of the pulser 26 in detail. Tubing 28 is attached (not shown) to a source of compressed or pressurized air or gas. A quick action valve 30 allows a rapid blast of pressurized air or gas to enter the cylinder 50 of the pulser 26. Within the cylinder 50 there is a projectile 52 that can freely slide therein. At the other end of the pulser 26 there is a spring loaded slidable plunger comprising a plunger rod 32 and a spring 56. The cylinder 50 of the pulser 26 is enlarged at 58 to accommodate, and retain the spring 56. Within the wall of the pulser 26 there are vents 60 that allow pressure to escape. In use, the spring loaded plunger is tensibily placed against the roll surface 22 with an intervening sensor 34.

Figure 3:
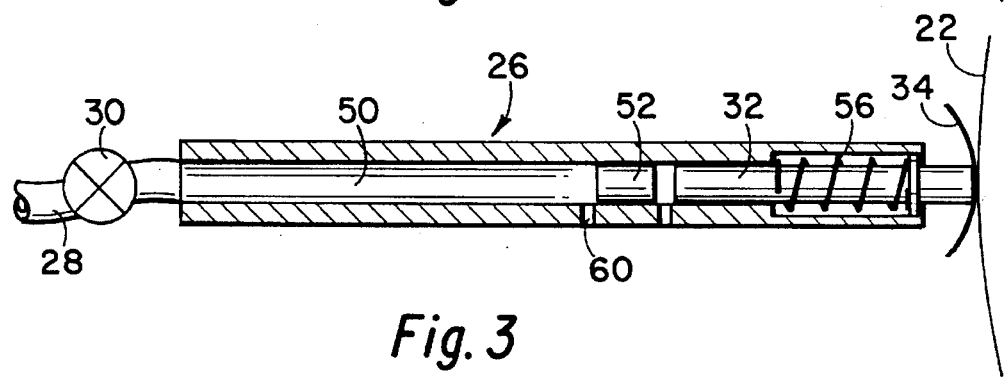
FIG. 3 is a cross-sectional sideview of the pulser with projectile in the "fired" position.

FIG. 2 and FIG. 3 are similar, with the projectile 52 in the "cocked" position in FIG. 2 and in the "fired" position in FIG. 3. To "cock" the pulser 26, it is tipped downward so that the air tubing end is lower than the plunger end—this causes the projectile 52 to slide to the air tubing end ready to be fired.

Other means of "firing" the pulser 26 may be used—such as explosive devices, impact devices, electromagnetic power means and the like. The projectile 52 is closed fitted to slide easily with the cylinder 50 of the pulser 26. The vents 60 allow air to escape when the projectile 52 is fired, so that pressure will not build up in front of the projectile and is relieved in back of the projectile just prior to impact with the plunger 32. The pulser 26 must provide sufficient energy at impact to produce a high frequency (e.g. 100 kHz–1 mHz), sharp wave depending upon web material.

Various tests were done with the above described invention. In one series of tests, stacks of web materials, i.e. papers and plastic films, were tested in a materials testing system (an Instron Model 8502 was used) which showed that material density changed very little with pressure and therefore could be considered constant. The stack tests also showed that the radial modulus of a web stack could be modeled as a polynomial function of pressure. Most material could be modeled using the following equation (1):

$$E_r = C_1 \times P \tag{1}$$

$E_r$=radial modulus, Pa (1 psi=6.895×10³ Pa)

$C_1$=slope of the $E_r$ vs. P curve (dimensionless)

P=pressure, Pa (1 psi=6.895×10³ Pa)

The theoretical speed of sound in a solid is given by the following equation (2):

$$c = \sqrt{\frac{E}{\rho}} \tag{2}$$

c=wave propagation speed (meters/second)

E=Young's modulus, Pa (1 psi=6.895×10³ Pa)

ρ=density, Kg/m³ (1 lb/in.³=3.613×10⁻⁵ Kg/m³)

By replacing E with $E_r$ and using a constant density ρ, the wave speed in the test stacks could be determined.

The mechanical pulser (described above) releases about 1 joule of energy in 3.3 μs (300 kHz). A pressure wave is generated as described by the following equation (3):

$$P = \rho \times c \times V \tag{3}$$

P=Pressure, Pa

ρ=Density, Kg/m³ c=Wave propagation speed, m/s

V=Projectile Velocity, m/s the duration of the pressure wave (as given in the preceding equation) is equal to the time required for the wave to travel from the point of impact to the other end of the projectile bar and back, as described by the following equation (4):

$$t = \frac{2 \times l}{c} \tag{4}$$

t=time (seconds)

c=wave propagation speed, m/s l=Projectile length (meters)

Figure 4:
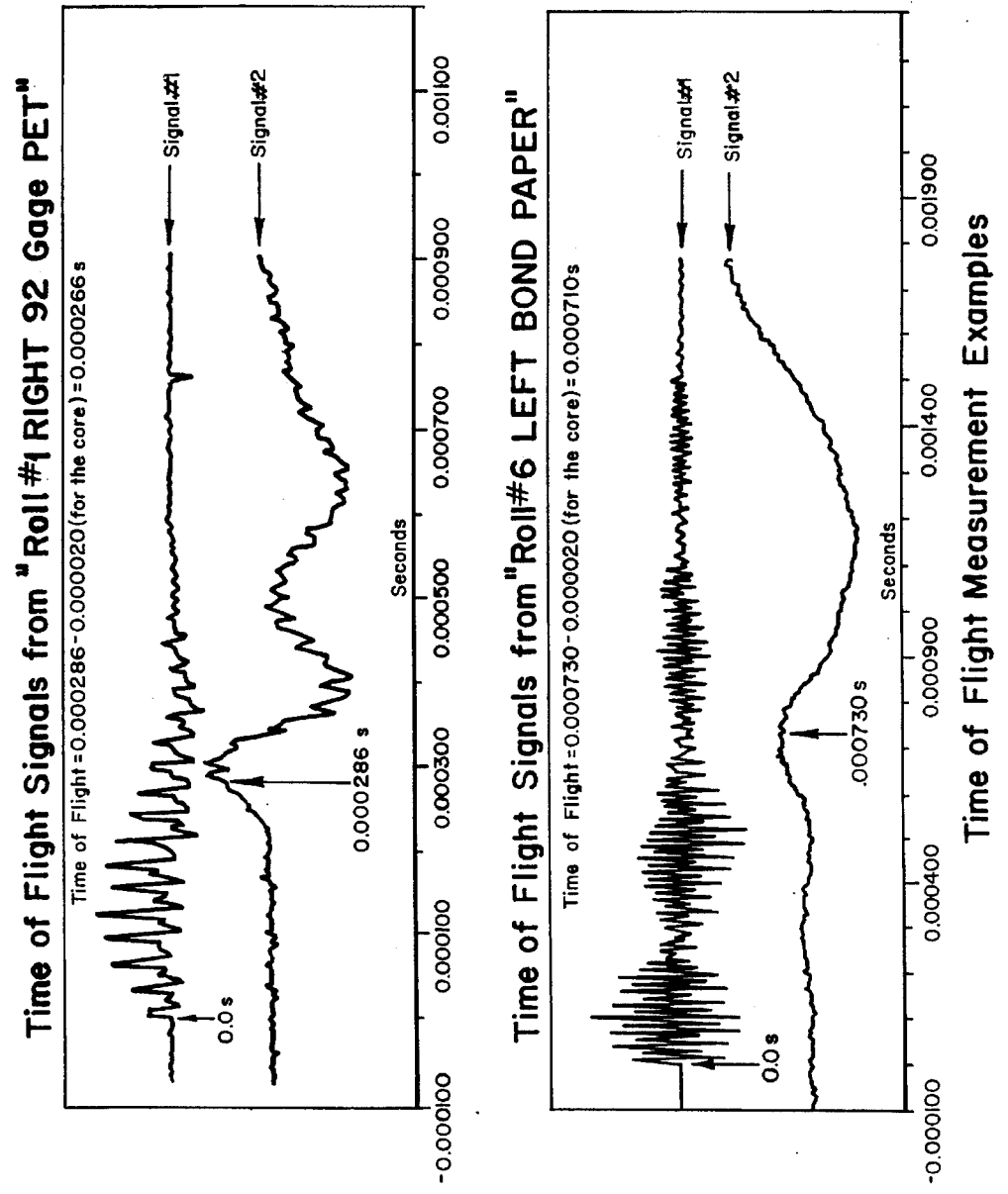
FIG. 4 is graphic examples of normalized signals and time of flight measurements used to determine roll structure.

The next step was to determine the time of flight (TOF) through a roll of material such as a bond paper and 92 gauge polyester (PET). To determine the time of flight (TOF), the wave must be initiated and received at known times. In this instance to determine the initiation time of the wave occurred by placing the KYNAR film sensor between the pulser pressure bar and the roll. When the pulser is fired, the sensor produces a voltage signal as the wave travels from the pressure bar through the film sensor and into the roll. The signal from the sensor goes directly into oscilloscope. As it turns out, this signal is very clean and has amplitude of several volts. The scope is direct current (DC) coupled and triggered at a level above the noise, but well below the peak amplitude of the signal. The actual trigger level is not important because of the extremely fast rise time of the signal. The signal is received with a simple accelerometer or KYNAR sensor and held against the inside of the core, and often requires very little amplification or filtering. Ordinarily, the determination of the exact time the wave has been received is difficult because of the low frequency and small band width of the wave. The technique that worked best was to pick the first peak that was at least five standard deviations above the signal noise. In all cases tested the resulting algorithm produced very reasonable time of flight values such as shown in FIG. 4.

The TOF measurement can be used in determining winding tension. To accomplish this, an arbitrary roll of material would be obtained from a warehouse. A stack of the aforesaid material is tested to determine the relationship between radial modulus and pressure would be performed. A theoretical winding model would be employed with an initial estimate of winding tension to produce a pressure profile that can be used with equations (1) and (2) to determine the speed of sound as a function of the radius of the roll. The speed of sound as a function of the radius can be integrated from the core to the outside of the roll to calculate the time of flight resulting from an initial estimate of winding tension. The difference between the calculated TOF and the actual measured TOF is then used to make a better estimate of the winding tension. This iteration process is continued until the calculated TOF converges with actual measured TOF. The resulting data provides information as to the roll structure, including radial pressure, circumferential stress and winding tension.

Another potential unknown or questionable model input is the radial modulus in cases in which it is difficult or impossible to perform stack tests for radial modulus. If the winding tension is known, then the TOF measurement can be used with equation (2) to determine the average radial modulus. This constant modulus can be used in models such as taught in the references of Altmann, Yagoda or Hakiel for use as a constant modulus roll structure gauge.

Figure 5:
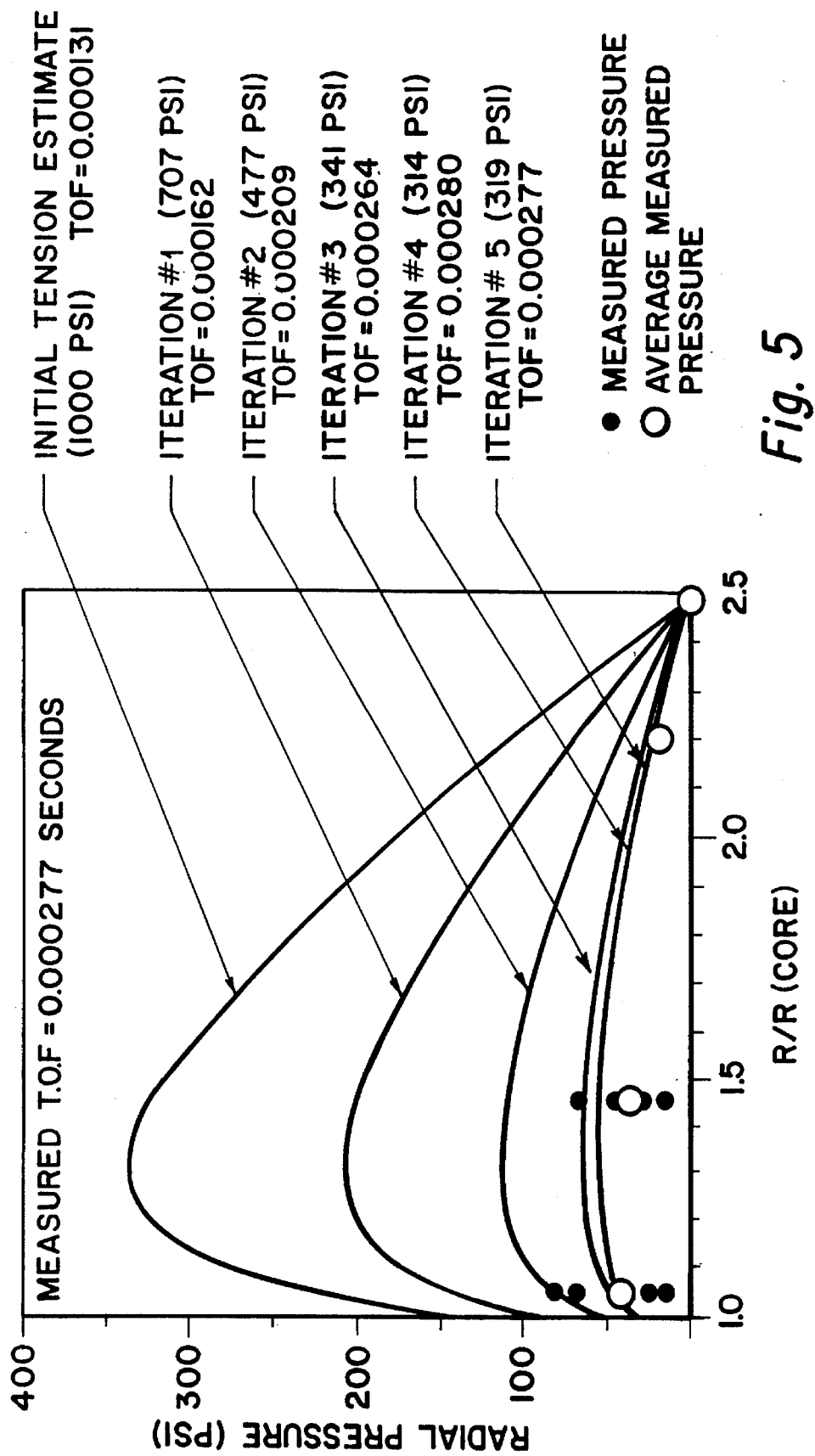
FIG. 5 is a graphic display of the wound roll internal stress computer experimental data.

A digital computer program was then written that reads the two signals from the oscilloscope. These two signals are processed according to criteria discussed earlier to determine the measured TOF. The program has two options: a constant $E_r$ and acoustic roll structure gage determined from the TOF model described above. If the constant $E_r$ is selected the TOF measurement is used to calculate an average $E_r$, which is used in the model to replace the stack test $E_r$ function. The remaining model inputs, including $T_w$ (winding stress, Pa where 1 psi=$6.895 \times 10^3$ Pa), remain unchanged. The program and computer then calculates the roll structure, plots the radial pressure distribution and files the data. If the acoustic gage option is invoked, an initial guess of $T_w$ and the stack test $E_r$ function is used to calculate the radial pressure of the roll structure. This radial pressure and equations (1) and (2) are integrated to determine the calculated TOF and the calculated TOF is used to make a better estimate of the actual $T_w$. This iteration process continues until the difference between the measured and the calculated TOF is less than 1 μs. The roll structure data from the last iteration is then plotted and the data written to a file within the computer. The results of the experimentation described above is shown in FIG. 5. The measured data in FIG. 5 was collected using pull tabs and force sensitive resistors. Note the agreement between the average measured pressure data and iteration #5, in which the computed time of flight has converged upon the measured time of flight.

While the invention has been described with a certain degree of particularity it is manifest that many changes may be made in the details of construction and the arrangement of components without departing from the spirit and scope of this disclosure. It is understood that the invention is not limited to the embodiments set forth herein for purposes of exemplification, but is to be limited only by the scope of the attached claim or claims, including the full range of equivalency to which each element thereof is entitled.

What is claimed is:

1. An apparatus for measuring wave propagation through a wound roll of material, comprising:

means for generating a wave radially across said wound roll of material comprising;

a pulser tube with a hollow cylinder having a first end and a second end;

a spring-loaded plunger, having a first end and a second end, with the first end of said plunger projecting from said first end of said cylinder of said tube, and the second end of said plunger slidably retained within the cylinder of said tube at the first end of said tube;

a projectile slidably disposed within the cylinder of said tube which is freely moveable from said second end of said cylinder to a contact position with said second end of said plunger; and means to impel said projectile from said second end of said cylinder to the contact position with said second end of said plunger resulting in the generation of the wave;

a first detecting means for detecting said wave when said wave enters said wound roll of material and generating a signal therefrom;

a second detecting means for detecting said wave when said wave has traveled through said wound roll of material and generating a signal therefrom; and means for analyzing said signals from said first and second detecting means and measuring wave propagation therefrom.

2. The apparatus as described in claim 1 wherein said means to impel said projectile is compressed gas.

3. The apparatus of claim 1, wherein said wound roll includes an external surface and a hollow core, and said generated wave is directed radially through said wound roll.

4. The apparatus of claim 3 wherein said first detecting means is placed on the external surface of said roll and said second detecting means is placed within said hollow core of said roll.

5. The apparatus of claim 1 wherein said first detecting means is a piezoelectric sensor.

6. The apparatus of in claim 1 wherein said second detecting means is a piezoelectric sensor.

7. The apparatus of in claim 1 wherein said second detecting means is an accelerometer.

8. The apparatus as described in claim 1, wherein said analyzing means is an oscilloscope.

9. The apparatus as described in claim 1, wherein said analyzing means is a computer.

10. The apparatus of claim 1 wherein said means to impel said projectile is electromagnetically powered.

\* \* \* \* \*